United States Patent [19]

Phillips et al.

[11] 4,413,143

[45] Nov. 1, 1983

[54] METHOD OF PRODUCING ACRYLAMIDE FROM WATER-IN-OIL EMULSION OF ACRYLONITRILE

[75] Inventors: Kenneth G. Phillips, River Forest; John G. Premo, Western Springs, both of Ill.

[73] Assignee: Nalco Chemical Company, Oak Brook, Ill.

[21] Appl. No.: 329,011

[22] Filed: Dec. 9, 1981

Related U.S. Application Data

[63] Continuation of Ser. No. 213,278, Dec. 5, 1980, which is a continuation of Ser. No. 89,817, Oct. 31, 1979, abandoned.

[51] Int. Cl.$^3$ ............................................. C07C 102/08
[52] U.S. Cl. .................................. 564/128; 252/309
[58] Field of Search ....................... 252/309; 564/128; 260/29.6 WQ

[56] References Cited

U.S. PATENT DOCUMENTS

| | | | |
|---|---|---|---|
| 3,284,393 | 11/1966 | Vandernoff et al. | 260/29.6 HN |
| 3,624,019 | 11/1971 | Anderson et al. | 260/29.6 H |
| 3,920,740 | 11/1975 | Svarz et al. | 260/561 N |
| 3,923,756 | 12/1975 | Svarz et al. | 526/240 |
| 3,997,492 | 12/1976 | Kane et al. | 260/29.6 WQ |

*Primary Examiner*—Paul F. Shaver
*Attorney, Agent, or Firm*—John G. Premo; Robert A. Miller; John S. Roberts, Jr.

[57] ABSTRACT

A method of producing acrylamide from acrylonitrile in the presence of a metallic conversion catalyst which comprises contacting a water-in-oil emulsion of acrylonitrile which is contained in the dispersed aqueous phase of the emulsion under conditions whereby a substantial portion of the acrylonitrile is converted to acrylamide which remains in the aqueous phase of the emulsion.

5 Claims, No Drawings

METHOD OF PRODUCING ACRYLAMIDE FROM WATER-IN-OIL EMULSION OF ACRYLONITRILE

This is a continuation of application Ser. No. 213,278, filed Dec. 5, 1980 which is a continuation of Ser. No. 89,817 filed Oct. 31, 1979 now abandoned.

INTRODUCTION

It is now known that acrylamide can be produced by reacting acrylonitrile with water in the presence of a metallic conversion catalyst. These catalytic processes are now being used on a commercial scale. It is common in these processes to react about 7% acrylonitrile dissolved in water in the presence of these metallic catalysts whereby a dilute aqueous solution of acrylamide is produced. These solutions of acrylamide may be polymerized to form water-soluble polymers and copolymers by using a water-in-oil emulsion polymerization technique. This technique is described generally in Vanderhoff U.S. Pat. No. 3,284,393, the disclosure of which is incorporated herein by reference.

The conversion of acrylonitrile to acrylamide as described produces a dilute aqueous solution of acrylamide. These solutions require concentration in order to effectively produce a commercial form of the water-in-oil emulsions which contain the polymers.

If it were possible to prepare relatively concentrated water-in-oil emulsions of acrylamide directly from acrylonitrile, substantial savings would be made in the costs of converting acrylamide into its polymers and copolymers by the water-in-oil polymerization techniques previously described.

THE INVENTION

A method of producing acrylamide from acrylonitrile in the presence of a metallic conversion catalyst which comprises contacting a water-in-oil emulsion of acrylonitrile which is contained in the dispersed aqueous phase of the emulsion under conditions whereby a substantial portion of the acrylonitrile is converted to acrylamide, which acrylamide remains in the aqueous phase of the emulsions.

In a preferred embodiment of the invention the catalyst used is a finely divided metallic copper catalyst having a high degree of activity and, most preferably, a Raney copper catalyst which contains 2–45% by weight of aluminum. In another embodiment of the invention, it is possible to incorporate into the acrylonitrile water-in-oil emulsion sufficient amounts of caustic such as sodium hydroxide or carbonate to convert by hydrolyzing the acrylonitrile or the produced acrylamide to sodium acrylate.

The Metallic Nitrile Conversion Catalyst

During the last several years, numerous metallic catalysts for converting nitrile and water into amides have been patented or described in the literature. A summary of these catalysts as well as literature references thereto is set forth below:

| Catalyst | Literature Reference |
| --- | --- |
| Raney copper, Ullman copper, reduced copper, copper on a carrier, silver cobalt, nickel, palladium and platinum. | Canadian Patent 899,380 |
| Copper in combination with nickel, chromium manganese, zinc, molybdenum, as well as oxides or sulfides of said metal. | Canadian Patent 930,377 |
| Combinations consisting essentially of 10 to 90% by weight of oxides of copper, silver, zinc or cadmium and 10 to 90% by weight of oxides of chromium or molybdenum. | U.S. Pat. No. 3,597,481 |
| Urushibara - copper chloride precipitate with zinc dust. | Watanabe in Bull. Chem., Soc. Japan, 37.1325 (1964) |
| Copper, copper oxide, copper-chromium oxide, copper-molybdenum oxide or mixtures thereof. | U.S. Pat. No. 3,631,104 |
| Reduced copper oxides in combination with other metal oxides, particularly rare earth metal oxides. | U.S. Pat. No. 3,696,152 |
| Copper prepared by reducing copper hydroxide or a copper salt. | U.S. Pat. No. 3,758,578 |
| Copper metal. | U.S. Pat. No. 3,767,706 |
| Highly active Raney copper. | U.S. Pat. No. 3,920,740 |
| Zinc and cadmium oxides. | German 551,869 |
| Lithium hydroxide. | U.S. Pat. No. 3,686,307 |
| Ruthenium, rhodium, palladium, osmium, iridium or platinum. | U.S. Pat. No. 3,670,021 |
| Fatty acid salts of cadmium, zinc, copper, cobalt, lead, tin, titanium, nickel, iron, mercury; sulfates, nitrates and halides of lead, tin, titanium, nickel, iron, mercury; tin, cadmium & copper oxides; copper powders. | Jap. 70/21,295. Inoue et al., Ashi Kasei Co., 7-18-70. |
| Cupric hydroxide, manganese dioxide, chromium, tungsten, iron or nickel oxide. | Japan 72/33,327 |
| Boron hydroxide & inorganic phosphorous containing acids. | Japan 73/36118 |
| Cobalt chromium catalyst. | Japan 73/39424 |
| Nickel chromium catalyst. | Japan 73/39426 |
| Ruthenium or rhodium. | Japan 73/54,021 |
| Manganese dioxide. | Haefele et al., Ind. Eng. Chem. Prod. Res. Develop. 11(3), 364–365 (1972) |
| Zinc, copper cobalt & cadmium thiocyanates, sulfates, nitrates, halides and cyanides as well as metallic zinc and metallic copper. | Spanish Patent Appl. Public No. 695205 |
| Metal salts of cation exchange resins. | U.S. Pat. No. 3,674,848 |
| Cuprous dihydrogen phosphate. | U.S. Pat. No. 3,679,745 |
| Copper salts. | U.S. Pat. No. 3,381,034 |

Of the above catalysts, I prefer to use in the practice of my invention a special Raney copper catalyst which contains from about 2 to 45% by weight of aluminum. This catalyst in its preferred embodiment contains particles having an average particle diameter ranging from 0.002 to 0.5 inches and has a relative activity of at least about 2. Catalysts of this type as well as their method of preparation are disclosed in U.S. Pat. No. 3,920,740, the disclosure of which is incorporated herein by reference.

As will be shown hereafter, it is important that the metallic catalyst be capable of producing acrylamide from acrylonitrile and water in yields of at least 30% and, preferably, at least 50%. In certain instances, certain of the catalysts listed above are incapable of producing acrylamide in such yields under normal commercial operating conditions. It is understood, therefore, that only those catalysts capable of producing acrylamide in a 30% yield are intended to be included in my definition of a metallic conversion catalyst.

The Water-in-Oil Emulsions of Acrylonitrile

The components of the emulsions are listed below in terms of their weight percentages:

A. Acrylonitrile:
 1. Generally from 5–60%;
 2. Preferably from 20–40%; and
 3. Most preferably from 25–35%;

B. Water:
 1. Generally from 20–90%;
 2. Preferably from 20–70%; and
 3. Most preferably from 30–55%;

C. Hydrophobic liquid:
 1. Generally from 5–75%;
 2. Preferably from 5–40%; and
 3. Most preferably from 20–30%; and D. Water-in-oil emulsifying agent:
 1. Generally from 0.1–21%;
 2. Preferably from 1–15%;
 3. Most preferably from 1.2–10%.

In the above, the general range of acrylonitrile in the emulsion is shown to be 5–60%. This concentration of acrylonitrile can be achieved in the aqueous phase of the emulsion even though it is only soluble in water up to about 7% by weight. It is contemplated that the emulsions can be a dispersion of acrylonitrile at the beginning of the reaction but the nitrile would be rapidly solubilized into the water as it was converted to acrylamide. Acrylamide-water solutions tend to form a solvent system for acrylonitrile. This is demonstrated below in Table I.

TABLE I

| Nitrile Solubility | |
|---|---|
| Percent by Weight of Acrylamide Solution | Percent by Weight of Nitrile in Solution Based on Water |
| 0 | 7 |
| 10 | 12.99 |
| 20 | 16.0 |
| 40 | 58.66 |
| 50 | 185.6 |
| 60 | 246.0 |

As indicated, in certain instances it is desirable that the acrylonitrile emulsions, in addition to their conversion catalyst, also contain amounts of alkali metal calculated to convert varying amounts of the nitrile and/or acrylamide to sodium acrylate. The presence of the alkali also enhances the solubility of the nitrile in the aqueous phase of the emulsion as the conversion of the nitrile to the amide progresses.

It is also possible to further characterize the water-in-oil emulsions of acrylonitrile with respect to the aqueous phase of the emulsions. This aqueous phase is generally defined as the sum of the acrylonitrile present in the emulsion plus the amount of water. This terminology may also be utilized in describing the water-in-oil emulsions which are useful in this invention. Utilizing this terminology, the aqueous phase of the water-in-oil emulsions of this invention generally consists of 25–95% by weight of the emulsion. Preferably, the aqueous phase is between 60–90% and, most preferably, from 65–85% by weight of the emulsion.

The emulsions also may be characterized in relation to the water/oil ratios. This figure is simply a ratio of the amount of water present in the emulsion divided by the amount of hydrophobic liquid present in the emulsion. Generally, the water-in-oil emulsions of this invention will have a water/oil ratio of from 0.25 to 18. Preferably, the water-in-oil ratio will range from 0.5–14 and, most preferably, from 1.0–2.75.

The Hydrophobic Liquids

The hydrophobic liquids or oils used in preparing these emulsions may be selected from a large group of organic liquids which include liquid hydrocarbons and substituted liquid hydrocarbons.

A preferred group of organic liquids that can be utilized in the practice of this invention are paraffinic hydrocarbon oils. Examples of these types of materials include a branch-chain isoparaffinic solvent sold by Humble Oil and Refinery Company under the tradename "Isopar M" described in U.S. Pat. No. 3,624,019, and a paraffinic solvent sold by the Exxon Company, U.S.A. called "Low Odor Paraffinic Solvent." Typical specifications of this material are set forth below in Table II.

TABLE II

| | |
|---|---|
| Specific Gravity 60°/60° F. | 0.780–0.806 |
| Color, Saybolt | +30 min. |
| Appearance, visual | Bright and Clear |
| Aniline Point, °F., ASTM D-611 | 160 min. |
| Distillation, °F., ASTM D-86 | |
| IBP | 365 min. |
| FBP | 505 max. |
| Flash Point, °F., TCC | 140 min. |
| Sulfur, ppm, Microcoulometer | 15 max. |

While paraffinic oils are the preferred materials for use in preparing the water-in-oil emulsions of this invention, other organic liquids can be utilized. Thus, mineral oils, kerosenes, naphthas, and, in certain instances, petroleum may be used. While useful in this invention, solvents such as benezene, xylene, toluene, and other water immiscible hydrocarbons having low flash points or toxic properties are generally avoided due to problems associated with their handling.

The Water-in-Oil Emulsifying Agents

Any conventional water-in-oil emulsifying agent can be used such as sorbitan monostearate, sorbitan monooleate, and the so-called low HLB materials which are all documented in the literature and are summarized in the Atlas HLB Surfactants Selector. Although the mentioned emulsifiers are used in producing good water-in-oil emulsions, other surfactants may be used as long as they are capable of producing these emulsions. It is also contemplated, however, that other water-in-oil emulsifying agents can be utilized.

United States Pat. No. 3,997,492 shows the use of emulsifiers generally having higher HLB values to produce stable emulsions. With the use of the equations present in this reference, which is hereinafter incorporated by reference, emulsifiers having HLB values between 4–9 can be utilized in the practice of this invention.

As indicated, it is possible to conduct the conversion of the acrylonitrile to acrylamide in the presence of an alkali such as sodium hydroxide or carbonate which converts a portion of the nitrile or amide groups to sodium acrylate groups. The rate of caustic hydrolysis of acrylonitrile sodium acrylate is described in the work, *The Chemistry of Acrylonitrile,* American Cyanamid Company, 1959, Page 11 and 258[1]. For the alkaline hydrolysis of acrylamide, reference should be made to the publication, *Chemistry of Acrylamide,* American Cyanamid Company, 1969, Page 7. These publications are incorporated herein by reference.

[1] 737. Mamiya J. Soc. Chem. Ind. Japan 44,860 (1941).

One of the interesting features of the invention is that when the emulsions of the acrylonitrile are prepared using sufficient quantities of low HLB water-in-oil emulsion agents, the acrylamide produced remains in the aqueous phase of the water-in-oil emulsion. In this form it can be utilized directly in the water-in-oil polymerization system previously described.

Conversion Conditions

As a general rule, the conversion of the acrylonitrile to acrylamide may be conducted at temperature ranges from 150°–300° F. with temperatures in the range of 160°–250° being preferred. The preferred catalyst is a Raney copper catalyst of the type described in U.S. Pat. No. 3,920,740, the disclosure of which is incorporated by reference. This patent also shows additional reaction conditions that may be used. While I prefer to use a metallic catalyst such as Raney copper or reduced copper catalyst of the type already described, it is to be understood that homogeneous catalysts, e.g. those which are soluble in water, may be used. Such catalysts would be amine complexes of copper. In such complexes, the copper must be in the zero valence state.

EXAMPLE 1

The process of our invention for converting water-in-oil emulsions of acrylonitrile to water-in-oil emulsions of acrylamide would be expected to function in the following manner:

A. Forming an emulsion which comprises from 20–40% by weight of acrylonitrile, from 20–70% by weight of water, from 5–40% by weight of a hydrophobic liquid, and from 1–15% by weight of a water-in-oil emulsifying agent having a relatively low HLB. These emulsions would be formed by adding the components mentioned above in any order to a vessel which was equipped with a nitrogen blanket, a vigorous agitator, and means for controlling temperature and pressure. After the components have been added, vigorous agitation of the mixture will be anticipated to form the emulsions of the instant invention.

B. Once the above emulsions have been formed, the emulsions so formed may be converted to acrylamide in a water-in-oil emulsion by passing said acrylonitrile emulsions formed in the initial step through a catalyst bed which is capable of converting acrylonitrile to acrylamide. Another method which is anticipated is the addition of a preferred catalyst which may accomplish said conversion of acrylonitrile to acrylamide directly into the agitated vessel mentioned above.

C. The original acrylonitrile emulsion formed in Step A above, may then be reacted with the chosen catalyst of Step B at temperatures ranging from 160°–250° F. for a period of time sufficient to accomplish the conversion of acrylonitrile to acrylamide.

It would be expected that emulsions containing 30+ or −5% by weight acrylonitrile, 42.5+ or −7.5 weight percent water, 25+ or −5 weight percent of a hydrophobic liquid, preferably either low odor paraffinic solvent or a branch chained isoparaffinic solvent represented by the Trademark ISOPAR M, and 5+ or −3.5% of a low HLB emulsifying agent, such as sorbitan monostearate, sorbitan monooleate, or any emulsifier having an HLB value between 4 and 9 could be utilized in the formation of the stable water-in-oil emulsions of acrylonitrile.

This mixture would then be vigorously agitated, protected from oxidizing atmospheres by an inert gas blanket, and either continuously or in a batch manner exposed to a copper based catalyst system, such as the preferred Raney copper catalyst described in U.S. Pat. No. 3,920,740, such exposure to the catalyst being accomplished in a temperature range from 160° F. to 250° F. until which time a substantial portion of the acrylonitrile present in the original water-in-oil emulsions of acrylonitrile is inverted to acrylamide, thus forming stable water-in-oil emulsions of acrylamide which may be used in subsequent steps to form polymers.

EXAMPLE 2

It would be anticipated that 25 weight percent acrylonitrile, 40 weight percent water, 30 weight percent LOPS, and 5 weight percent sorbitan monostearate when added together in a vessel equipped as in Example 1 and vigorously agitated would form a stable acrylonitrile water-in-oil emulsion. This emulsion would contain acrylonitrile in both the organic and the aqueous phase of the emulsion.

We would anticipate taking the emulsions so formed to a temperature not exceeding 300° F. but at least 150° F. prior to exposure of this stabilized emulsion to a catalyst system capable of converting acrylonitrile to acrylamide in an efficacious manner.

It is anticipated that the water-in-oil emulsion containing acrylonitrile in both phases would then be pumped through a catalyst bed comprising a Raney copper catalyst as described in Example 1. A recirculating system could be used to accomplish the gradual conversion of acrylonitrile to acrylamide and simultaneously accomplish the concentration build-up of acrylamide and acrylonitrile in the water phase of the resultant stable emulsion. This recirculation system would be operated at the temperatures mentioned above for a time sufficient to convert a substantial quantity of acrylonitrile to acrylamide.

The resulting product would be anticipated to be a stable water-in-oil emulsion containing acrylamide and perhaps trace quantities of unconverted acrylonitrile. This final emulsion product could be further treated by the addition of caustic to convert a portion of the acrylamide to acrylic acid via a simple hydrolysis reaction. Depending upon how much anionic character a subsequent polymer might be desired to contain, this subsequent caustic addition could be controlled. Following the formation of the stable acrylamide emulsion, it is fully anticipated that the addition of a catalyst system of the free radical type or a catalyst system of the redox free radical type could accomplish the polymerization of this monomer containing emulsion via techniques generally outlined in U.S. Pat. No. 3,284,393, the disclosure of which is incorporated herein by reference. Following polymerization the products obtained would be expected to be a stable water-in-oil emulsion containing polyacrylamide or copolymers derived from polyacrylamide and acrylic acid.

Having thus described our invention, it is claimed as follows:

1. A method of producing acrylamide from acrylonitrile in the presence of a metallic conversion catalyst which comprises contacting a water-in-oil emulsion of acrylonitrile which is contained in the dispersed aqueous phase of the emulsion under conditions whereby a substantial portion of the acrylonitrile is converted to acrylamide which remains in the aqueous phase of the emulsion.

2. The method of claim 1 where the conversion catalyst is a finely divided catalystically active species of copper.

3. The method of claim 2 where the finely dispersed conversion catalyst is a Raney copper catalyst which contains from about 2-45% by weight of aluminum.

4. The method of claim 1 where the conversion of acrylonitrile to acrylamide is done in the presence of sufficient sodium hydroxide to convert from 1-50% by weight of the nitrile and/or amide group to sodium acrylate groups.

5. The method of claim 1 where the metallic conversion catalyst is a homogeneous catalyst.

* * * * *